(12) United States Patent
Urch et al.

(10) Patent No.: US 6,174,894 B1
(45) Date of Patent: Jan. 16, 2001

(54) BICYCLIC AMINE DERIVATIVES

(75) Inventors: Christopher John Urch; Terence Lewis; Raymond Leo Sunley; Roger Salmon; Christopher Richard Ayles Godfrey; Christopher Ian Brightwell, all of Bracknell (GB)

(73) Assignee: Zeneca Limited, London (GB)

( * ) Notice: Under 35 U.S.C. 154(b), the term of this patent shall be extended for 0 days.

(21) Appl. No.: 09/357,749

(22) Filed: Jul. 21, 1999

Related U.S. Application Data

(62) Division of application No. 08/969,639, filed on Nov. 13, 1997, now Pat. No. 6,093,726.

(30) Foreign Application Priority Data

Nov. 26, 1996 (GB) .................................................... 9624611

(51) Int. Cl.$^7$ ...................... A61K 31/435; A61K 31/439; C07D 471/08
(52) U.S. Cl. .......................... 514/299; 546/112; 546/124; 546/183; 514/304
(58) Field of Search .................................. 514/299, 304; 546/112, 124, 125, 127, 183

(56) References Cited

U.S. PATENT DOCUMENTS

| | | | |
|---|---|---|---|
| 3,120,537 | 2/1964 | Archer et al. | 260/291 |
| 3,133,073 | 5/1964 | Archer | 260/292 |
| 3,308,131 | 3/1967 | McKusick | 260/294 |
| 3,501,461 | 3/1970 | Newallis et al. | 260/239 |
| 3,546,232 | 12/1970 | Kaiser et al. | 260/292 |
| 3,556,943 | 1/1971 | Fonken et al. | 195/51 |
| 3,657,257 | 4/1972 | Helsley et al. | 260/292 |
| 4,180,669 | 12/1979 | Winn | 546/240 |
| 4,393,069 | 7/1983 | Langbein et al. | 424/265 |
| 4,590,270 | 5/1986 | Kompis et al. | 544/320 |
| 4,774,249 | 9/1988 | Kompis et al. | 514/272 |
| 5,491,148 | 2/1996 | Berger et al. | 514/305 |
| 5,731,317 | * | 3/1998 | Lu et al. | 514/289 |

FOREIGN PATENT DOCUMENTS

| | | |
|---|---|---|
| 27 49 584 | 5/1978 | (DE) . |
| 0 031 219 | 7/1981 | (EP) . |
| 0 216 625 | 4/1987 | (EP) . |
| 0 307 142 | 3/1989 | (EP) . |
| 0 315 390 | 5/1989 | (EP) . |
| 0 398 578 | 11/1990 | (EP) . |
| 0 498 331 | 8/1992 | (EP) . |
| 0 518 805 | 12/1992 | (EP) . |
| 2 548 666 | 1/1985 | (FR) . |
| 1 061 472 | 3/1967 | (GB) . |
| 1 304 649 | 1/1973 | (GB) . |
| 91/17156 | 11/1991 | (WO) . |
| 92/01688 | 2/1992 | (WO) . |
| 93/00313 | 1/1993 | (WO) . |
| 93/14636 | 8/1993 | (WO) . |
| 93/25527 | 12/1993 | (WO) . |
| 95/03306 | 2/1995 | (WO) . |
| 96/08968 | 3/1996 | (WO) . |
| 96/36637 | 11/1996 | (WO) . |
| 96/37494 | 11/1996 | (WO) . |
| 97/13770 | 4/1997 | (WO) . |
| 97/43286 | 11/1997 | (WO) . |

OTHER PUBLICATIONS

Archer, S., et al., J. Am. Chem. Soc., "The Action of Nucleophilic Agents on 3 α–Chlorotropane," vol. 80, 1958, pp. 4677–4681.

(List continued on next page.)

* cited by examiner

Primary Examiner—Charanjit S. Aulakh
(74) Attorney, Agent, or Firm—Liza D. Hohenschutz

(57) ABSTRACT

The present invention provides a compound of Formula (I):

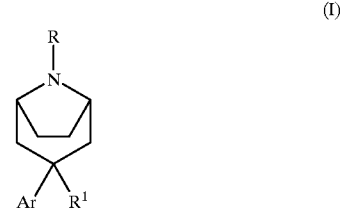

(I)

wherein Ar is optionally substituted phenyl wherein the substutuents, if present, are selected from halogen atoms, cyano, alkyl, alkenyl, alkynyl, alkoxy, haloalkyl, haloalkenyl, alkylthio and alkyl amino groups; R represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl or $XR^3$ (where X represents oxygen or a group $NR^4$); $R^3$ and $R^4$ are, independently, hydrogen, alkyl, aryl, heteroaryl, aralkyl, heteroarylalkyl, alkenyl, aralkenyl, alkynyl, heterocyclylalkyl, alkoxycarbonyl or carboxylic acyl each of which may be optionally substituted; $R^1$ represents hydrogen, hydroxy, alkyl, alkoxy, amino, nitro, isocyanato, acylamino, hydroxyalkyl, optionally substituted heteroaryl, alkoxyalkyl, haloalkyl, halohydroxyalkyl, aralkyloxyalkyl, acyloxyalkyl, amidoximido, sulfonyloxyalkyl, aminoalkyl, alkoxycarbonylamino, acylaminoalkyl, cyanoalkyl, imino, formyl, acyl or carboxylic acid or an ester or amide thereof, or alkenyl or alkynyl either of which is optionally substituted; or an acid addition salt, quaternary ammonium salt or N-oxide derived therefrom; an insecticidal, acaricidal or nematicidal composition comprising a compound of formula (I) and a suitable carrier or diluent therefor; and a method of combating and controlling insect, acarine or nematode pests at a locus which comprises treating the pests or the locus of the pests with an effective amount of a compound of formula (I) or a composition as hereinbefore described.

9 Claims, No Drawings

OTHER PUBLICATIONS

Bell, M.R., et al., J. Am. Chem. Soc., "Ethyl 3α–Phenyltropane–3β–carboxylate and Related Compounds," vol. 82, No. 7–9, 1960, pp. 4638–4641.

Cignarella, G., et al., J. Am. Chem. Soc., "A New Synthesis of Tropane Derivatives," vol. 83, No. 10–12, 1961, pp. 4999–5003.

Daum, S.J., et al., J. Med. Chem., "Analgesic Activity of the Epimeric Tropane Analogs of Meperidine. A Physical and Pharmacological Study," Vol. 18, No. 5, 1975, pp. 496–501.

Gutkowska, B., et al., Acta Polon. Pharm., "Syntezy Niektorych Pochodnych 8– Alkilo–8–Aza–Bicyklo[3.2.1] Oktan–3–Onu," vol. 38, No. 4, 1981, pp. 411–415.

Lowe, J.A., et al., J. Med. Chem., "Aza–Tricyclic Substance P Antagonists," vol. 37, No. 18, 1994, pp. 2831.

Maag, H., et al., Helvetica Chimica Acta, "94.5–(N–Arylnortropan–3–yl)– and 5–(N–Arylpiperidin–4–yl)–2,4–diaminopyrimidines, Noval Inhibitors of Dihydrofolate Reductase," vol. 69, No. 4, 1986, pp. 887–897.

Repke, D. B., et al., J. Org. Chem., "Abbreviated Ibogaine Congeners. Synthesis and Reactions of Tropan–3–yl–2– and –3–indoles. Investigation of an Unusual Isomerization of 2–Substituted Indoles Using Computational and Spectroscopic Techniques," vol. 59, No. 8, 1994, pp. 2164–2171.

Zirkle, C. L., et al., J. Org. Chem., "The Isomeric 3–Oxa– and 3–Thiagranatanin–7–ols and Their Derivatives; Reduction of Bicyclic Amino Ketones Related to Tropinone," vol. 26, 1961, pp. 395–407.

BICYCLIC AMINE DERIVATIVES

This application is a division of Ser. No. 08/969,639 filed Nov. 13, 1997 now U.S. Pat. No. 6,093,726.

This invention relates to novel bicyclic amine derivatives, to processes for preparing them, to insecticidal compositions comprising and to methods of using them to combat and control insect pests.

The invention provides a compound of formula (I):

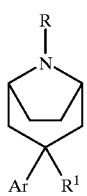

(I)

wherein Ar is optionally substituted phenyl or optionally substituted 5-or 6-membered heterocyclic ring containing from 1 to 3 heteroatoms individually selected from nitrogen, oxygen and sulfur atoms, and at least one unsaturation (double bond) between adjacent atoms in the ring, said heterocyclic ring being optionally fused to a benzene ring, wherein the substutuents, if present, are selected from halogen atoms, cyano, alkyl, alkenyl, alkynyl, alkoxy, haloalkyl, haloalkenyl, alkylthio and alkyl amino groups; R represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl or $XR^3$ (where X represents oxygen or a group $NR^4$), provided that when R is alkenyl, aralkenyl or alkynyl said group does not have an unsaturated carbon atom bonding directly to the ring nitrogen of formula (I); $R^3$ and $R^4$ are, independently, hydrogen, alkyl, aryl, heteroaryl, aralkyl, heteroarylalkyl, alkenyl, aralkenyl, alkynyl, heterocyclylalkyl, alkoxycarbonyl or carboxylic acyl; alkyl moieties of R, $R^3$ and $R^4$ comprise from 1 to 15 carbon atoms, and are optionally substituted with one or more substituents selected from halogen, cyano, carboxyl, carboxylic acyl, carbamyl, alkoxycarbonyl, alkoxy, alkylenedioxy, hydroxy, nitro, amino, acylamino, imidate and phosphonato groups; aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl or dithiocarboxyl moieties of R, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; $R^1$ represents hydrogen, hydroxy, alkyl, alkoxy, amino, nitro, isocyanato, acylamino, hydroxyalkyl, optionally substituted heteroaryl, alkoxyalkyl, haloalkyl, halohydroxyalkyl, aralkyloxyalkyl, acyloxyalkyl, amidoximido, sulfonyloxyalkyl, aminoalkyl, alkoxycarbonylamino, acylaminoalkyl, cyanoalkyl, imino, formyl, acyl or carboxylic acid or an ester or amide thereof, or alkenyl or alkynyl either of which is optionally substituted by halogen, alkoxy, cycloalkyl, optionally substituted aryl, optionally substituted heteroaryl or cyano; or an acid addition salt, quaternary ammonium salt or N-oxide derived therefrom.

It will be appreciated that the bicyclic amine compounds of formula (I) are capable of existing in more than one isomeric form since the groups Ar and $R^1$ may be positioned in either an exo or endo relationship, and the present invention embraces within its scope both exo and endo forms and mixtures thereof in all proportions and also any further isomeric variants arising from cis and trans substitution patterns or chiral centres present in either of Ar, R or $R^1$.

Examples of 5- and 6-membered heterocyclic ring systems represented by Ar include those based on pyridine, pyrazine, pyridazine, pirimidine, pyrrole, pyrazole, imidazole, 1,2,3- and 1,2,4-triazoles, furan, thiophene, oxazole, isoxazole, thiazole, isothiazole, 1,2,3- and 1,3,4-oxadiazoles, and 1,2,3- and 1,3,4-thiadiazoles, and partially reduced containing one double bond derived from these, as well as those based on oxathiole, dioxole, and dithiole rings containing one double bond. Preferably Ar represents a halo-substituted phenyl, pyridyl or diazinyl group.

When Ar is a 5- or 6- membered hererocyclic ring fused to a benzene ring then it is preferably benzoxazole, indole, benzofuran, benzothiophen or benzimidazole.

Halogen includes fluorine, chlorine, bromine and iodine.

Alkyl moieties preferably contain from 1 to 6, more preferably from 1 to 4, carbon atoms. They can be in the form of straight or branched chains, for example methyl, ethyl, n- or iso-propyl, or n-, sec-, iso- or tert-butyl.

Haloalkyl is preferably $C_{1-6}$ haloalkyl, especially fluoroalkyl (for example trifluoromethyl, 2,2,2-trifluoroethyl or 2,2-difluoroethyl) or chloroalkyl. For R, haloalkyl is preferably $C_{2-6}$ haloalkyl wherein there is no halogen on the a-carbon (for example 2,2,2-trifluoroethyl or 2,2-difluoroethyl).

Alkenyl and alkynyl moieties of $R^1$ and substituents of Ar preferably contain from 2 to 6, more preferably from 2 to 4, carbon atoms. They can be in the form of straight or branched chains, and, where appropriate, the alkenyl moieties can be of either (E)- or (Z)-configuration. Examples are vinyl, allyl and propargyl.

Aryl includes naphthyl but is preferably phenyl.

Heteroaryl includes 5- and 6-membered aromatic rings containing one, two, three or four heteroatoms selected from the list comprising oxygen, sulphur and nitrogen and can be fused to benzenoid ring systems. Examples of heteroaryl are pyridinyl, pyrimidinyl, pyridazinyl, pyrazinyl, triazinyl (1,2, 3-, 1,2,4- and 1,3,5-), furyl, thienyl, pyrrolyl, pyrazolyl, imidazolyl, triazolyl (1,2,3- and 1,2,4-), tetrazolyl, oxazolyl, isoxazolyl, thiazolyl, isothiazolyl, oxadiazolyl, thiadiazolyl, quinolinyl, isoquinolinyl, cinnolinyl, quinazolinyl, quinoxalinyl, indolinyl, isoindolinyl, benzofuranyl, benzothienyl and benzimidazolinyl.

The heterocyclyl part of heterocyclylalkyl is a ring containing one or two heteroatoms, selected from the list comprising oxygen, sulphur and nitrogen. Examples are piperidine, piperazine, pyrrolidine, tetrahydrofuran, morpholine, thietane, pyridine or thiazole.

The alkylenedioxy group is a substituent for a ring and is especially $C_{1-4}$ alkylenedioxy. Alkylenedioxy groups are optionally substituted with halogen (especially flourine) and are, for example, methylenedioxy ($OCH_2O$) or difluoromethylenedioxy ($OCF_2O$).

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids. Other examples of organic carboxylic acids include haloacids such as trifluoroacetic acid.

In one particular aspect the present invention provides a compound of formula (I), wherein Ar is optionally substituted phenyl or optionally substituted 5-or 6-membered heterocyclic ring containing from 1 to 3 heteroatoms individually selected from nitrogen, oxygen and sulfur atoms, and at least one unsaturation (double bond) between adjacent atoms in the ring, said heterocyclic ring being optionally fused to a benzene ring, wherein the substutuents, if present, are selected from halogen atoms, cyano, alkyl (especially $C_{1-4}$ alkyl), alkenyl (especially $C_{2-4}$ alkenyl), alkynyl (especially $C_{2-4}$ alkynyl), alkoxy (especially $C_{1-4}$ alkoxy), haloalkyl (especially $C_{1-4}$ haloalkyl), haloalkenyl (especially $C_{2-4}$ haloalkenyl), alkylthio (especially $C_{1-4}$ alkylthio), and alkyl amino (especially mono- or di- ($C_{1-4}$ alkyl)amino, such as mono- or di- ($C_{1-3}$ alkyl)amino) groups; R represents hydrogen or cyano or a group selected from alkyl (especially $C_{1-4}$ alkyl), aryl (especially phenyl), heteroaryl (especially pyridinyl or pyrimidinyl), aralkyl (especially aryl(C $C_{1-4}$)alkyl, such as phenyl($C_{1-4}$) alkyl), heteroarylalkyl (especially heteroaryl($C_{1-4}$)such as pyridinyl ($C_{1-4}$)alkyl or pyrimidinyl($C_{1-4}$ )alkyl), alkenyl (especially $C_{3-4}$ alkenyl), aralkenyl (especially aryl($C_{3-4}$)alkenyl, such as phenyl($C_{3-4}$)alkenyl), alkynyl (especially $C_{3-4}$ alkynyl), alkoxycarbonyl (especially $C_{1-4}$ alkoxycarbonyl), alkanesulfonyl (especially $C_{1-4}$ alkylsulfonyl), arenesulfonyl (especially phenylsulfonyl), alkenyloxycarbonyl (especially $C_{3-4}$ alkenyloxycarbonyl), aralkyloxycarbonyl (especially phenyl($C_{1-4}$)alkoxycarbonyl), aryloxycarbonyl (especially phenoxycarbonyl), heterocyclylalkyl (especially heterocyclyl($C_{1-4}$)alkyl, such as piperidinyl($C_{1-4}$)alkyl), carbamyl ($H_2NC(O)$), dithiocarboxyl or $XR^3$ (where X represents oxygen or a group $NR^4$), provided that when R is alkenyl, aralkenyl or alkynyl said group does not have an unsaturated carbon atom bonding directly to the ring nitrogen of formula (I); $R^3$ and $R^4$ are, independently, hydrogen, alkyl (especially $C_{1-4}$ alkyl), aryl (especially phenyl), heteroaryl (especially pyridinyl or pyrimidinyl), aralkyl (especially aryl($C_{1-4}$)alkyl, such as phenyl($C_{1-4}$)alkyl), heteroarylalkyl (especially heteroaryl($C_{1-4}$)alkyl, such as pyridinyl($C_{1-4}$)alkyl or pyrimidinyl($C_{1-4}$)alkyl), alkenyl (especially $C_{2-4}$ alkenyl), aralkenyl (especially aryl($C_{2-4}$) alkenyl, such as phenyl($C_{2-4}$)alkenyl), alknyl (especially $C_{2-4}$ alkynyl), heterocyclylalkyl (especially heterocyclyl($C_{1-4}$)alkyl, such as piperidinyl($C_{1-4}$)alkyl), alkoxycarbonyl (especially $C_{1-4}$ alkoxycarbonyl) or carboxylic acyl (especially $C_{1-4}$ alkylcarbonyloxy); alkyl moieties of R, $R^3$ and $R^4$ comprise from 1 to 15 carbon atoms, and are optionally substituted with one or more substituents selected from halogen, cyano, carboxyl (HOC(O)), carboxylic acyl (especially $C_{1-4}$ alkylcarbonyloxy), carbamyl ($H_2NC(O)$), alkoxycarbonyl (especially $C_{1-4}$ alkoxycarbonyl), alkoxy (especially $C_{1-4}$ alkoxy), alkylenedioxy (especially $C_{1-4}$ alkylenedioxy), hydroxy, nitro, amino, acylamino (especially $C_{1-4}$ alkylcarbonylamino), imidate ($C_{1-4}$ alkyl[C(O)NHC(O)]) and phosphonato (OP(OH)$_2$) groups; aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl moieties of R, $R^3$ and $R^4$ comprise from 1 to 15 carbon atoms, and are optionally substituted with one or more substituents selected from, halogen, cyano, carboxyl (HOC(O)), carboxylic acyl (especially $C_{1-4}$ alkylcarbonyloxy), carbamyl ($H_2NC(O)$), alkoxycarbonyl (especially $C_{1-4}$ alkoxycarbonyl), alkoxy (especially $C_{1-4}$ alkoxy), alkylenedioxy (especially $C_{1-4}$ alkylenedioxy), hydroxy, nitro, haloalkyl (especially $C_{1-4}$ haloalkyl), alkyl (especially $C_{1-4}$ alkyl), amino, acylamino (especially $C_{1-4}$ alkylcarbonylamino), imidate ($C_{1-4}$ alkyl[C(O)NHC(O)]) and phosphonato (OP(OH)$_2$) groups; $R^1$ is hydrogen, hydroxy, alkyl (especially $C_{1-4}$ alkyl), alkoxy (especially $C_{1-4}$ alkoxy), amino (especially unsubstituted, mono- or di-($C_{1-4}$)alkylamino or amino substituted with a formyl group), nitro, isocyanato, acylamino (especially $C_{1-4}$ alkylcarbonylamino or phenylcarbonylamino), hydroxyalkyl (especially monohydroxy($C_{1-4}$)alkyl), optionally substituted heteroaryl (especially tetrazole, oxadiazole, pyridinyl or pyrimidinyl optionally substituted by halogen, $C_{1-4}$ alkyl, $C_{1-4}$ haloalkyl, $C_{1-4}$ alkoxy or $C_{1-4}$ haloalkoxy), alkoxyalkyl (especially $C_{1-4}$ alkoxy($C_{1-4}$)alkyl), haloalkyl (especially $C_{1-4}$ haloalkyl), halohydroxyalkyl (especially $C_{1-4}$ halohydroxyalkyl, such as 2-hydroxy-1,1-difluoroethyl), aralkyloxyalkyl (especially phenyl($C_{1-4}$) alkoxy($C_{1-4}$)alkyl), acyloxyalkyl (especially $C_{1-4}$ alkylcarbonyloxy($C_{1-4}$ )alkyl), amidoximido ($C(NH_2)$NOH), sulfonyloxyalkyl (especially sulfonyloxy($C_{1-4}$) alkyl), aminoalkyl (especially amino($C_{1-4}$)alkyl), alkoxycarbonylamino (especially $C_{1-4}$ alkoxycarbonylamino), acylaminoalkyl (especially $C_{1-4}$ alkylcarbonylamino($CC_{1-4}$) alkyl or phenylcarbonylamino($C_{1-4}$)alkyl), cyanoalkyl (especially $C_{1-4}$ cyanoalkyl), imino (especially hydroxyimino (HON=CH) or $C_{1-4}$ alkoxyimino), formyl, acyl (especially $C_{1-4}$ alkylcarbonyl) or carboxylic acid or an ester (especially a $C_{1-4}$ alkyl ester) or amide (especially an unsubstituted or an N,N-di($C_{1-4}$)alkyl amide) thereof, or alkenyl (especially $C_{2-4}$ alkenyl) or alkynyl (especially $C_{2-4}$ alkynyl) either of which is optionally substituted by halogen, alkoxy (especially $C_{1-4}$ alkoxy), cycloalkyl (especially $C_{3-7}$ cycloalkyl, such as cyclopropyl or cyclohexyl), optionally substituted aryl (especially phenyl optionally substituted by halogen, $C_{1-4}$ alkyl, $C_{1-4}$ haloalkyl, $C_{1-4}$ alkoxy or $C_{1-4}$ haloalkoxy), optionally substituted heteroaryl (especially pyridinyl or pyrimidinyl optionally substituted by halogen, $C_{1-4}$ alkyl, $C_{1-4}$ haloalkyl, $C_{1-4}$ alkoxy or $C_{1-4}$ haloalkoxy) or cyano; or an acid addition salt, quaternary ammonium salt or N-oxide derived therefrom.

In a further aspect the present invention provides a compound of formula (Ia):

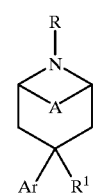

(Ia)

wherein A represents dimethylene; Ar represents an optionally substituted phenyl or 5-or 6-membered heterocyclic ring system containing from 1 to 3 heteroatoms individually selected from nitrogen, oxygen and sulfur atoms, and at least one unsaturation (double bond) between adjacent atoms in the ring, wherein the substutuents, if present, are selected from halogen atoms, alkyl, alkenyl, alkynyl, alkoxy, haloalkyl, haloalkenyl, alkylthio and alkyl amino groups, any of which groups contain up to six carbon, and wherein R represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbamyl or dithiocarboxyl groups, said groups comprising from 1 to 15 carbon atoms, said groups being optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; $R^1$ represents hydroxy, or a group selected from alkoxy, amino, acylamino, hydroxyalkyl, alkoxyalkyl, haloalkyl, halohydroxyalkyl, aralkyloxyalkyl, acyloxyalkyl, sulfonyloxyalkyl, aminoalkyl, acylaminoalkyl, cyanoalkyl, formyl, acyl, carboxylic acid and esters and amides thereof, alkenyl or alkynyl optionally substituted by halogen, alkoxy, aryl, heteroaryl or cyano; and acid addition salts and quaternary ammonium salts and N-oxides derived therefrom.

In a still further aspect the present invention provides a compound of formula (I), wherein Ar is pyridinyl (especially a pyridin-3-yl) optionally substituted by halogen (especially monosubstituted with chlorine or bromine), or phenyl optionally substituted by halogen (especially fluorine).

In another aspect the present invention provides a compound of formula (I), wherein Ar is phenyl, pyridinyl, pyridazinyl or pyrazinyl, all being optionally substituted with halogen (especially fluorine, chlorine or bromine), $C_{1-4}$ alkyl (especially methyl), $C_{1-4}$ alkoxy (especially methoxy), $C_{2-4}$ alkenyl, $C_{2-4}$ alkynyl or cyano.

In a further aspect the present invention provides a compound of formula (I) wherein R is $C_{1-4}$ alkyl (optionally substituted with cyano, $CO_2(C_{1-4}$ alkyl) or phenyl (itself optionally substituted with halogen, $C_{1-4}$ alkyl, $C_{1-4}$ alkoxy, $C_{1-4}$ haloalkyl or $C_{1-4}$ haloalkoxy)), $C_{2-4}$ haloalkyl (the α-carbon being unsubstituted), $C_{3-4}$alkenyl or $C_{3-4}$alkynyl; provided that when R is alkenyl or alkynyl said group does not have an unsaturated carbon atom bonding directly to the ring nitrogen of formula (I).

In yet another aspect the present invention provides a compound of formula (I), wherein R is $C_{1-4}$ alkyl (especially methyl), $C_{2-4}$ haloalkyl (the α-carbon being unsubstituted, especially $C_{2-4}$ fluoroalkyl, for example $CH_2CF_3$ or $CH_2CF_2H$) or $C_{1-4}$ alkoxycarbonyl (such as $CH_3CH_2OC(O)$ or $(CH_3)_3COC(O)$).

In a further aspect the present invention provides a compound of formula (I), wherein $R^1$ is alkyl (especially $C_{1-4}$ alkyl), amino (especially mono- or di-($C_{1-4}$) alkylamino), nitro, isocyanato, hydroxyalkyl (especially monohydroxy($C_{1-4}$)alkyl), alkoxyalkyl (especially $C_{1-4}$ alkoxy($C_{1-4}$)alkyl), haloalkyl (especially $C_{1-4}$ haloalkyl), halohydroxyalkyl (especially $C_{1-4}$ halohydroxyalkyl, such as 2-hydroxy-1,1-difluoroethyl), aralkyloxyalkyl (especially phenyl($C_{1-4}$)alkoxy($C_{1-4}$)alkyl), acyloxyalkyl (especially $C_{1-4}$ alkylcabonyloxy($C_{1-4}$)alkyl), alkoxycarbonylamino (especially $C_{1-4}$ alkoxycarbonylamino), acylamnoalkyl (especially $C_{1-4}$ alkylcarbonylamino($C_{1-4}$)alkyl or phenylcarbonylamino(C, )alkyl), cyanoalkyl (especially $C_{1-4}$ cyanoalkyl), acyl (especially $C_{1-4}$ alkylcarbonyl) or carboxylic acid or an ester (especially a $C_{1-4}$ alkyl ester) thereof, or alkenyl (especially $C_{2-4}$ alkenyl) or alkynyl (especially $C_{2-4}$ alkynyl) either of which is optionally substituted by halogen, alkoxy (especially $C_{1-4}$ alkoxy), cycloalkyl (especially $C_{3-7}$ cycloalkyl, such as cyclopropyl or cyclohexyl), optionally substituted aryl (especially phenyl optionally substituted by halogen, $C_{1-4}$ alkyl, $C_{1-4}$ haloalkyl, $C_{1-4}$ alkoxy or $C_{1-4}$ haloalkoxy), optionally substituted heteroaryl (especially pyridinyl or pyrimidinyl optionally substituted by halogen, $C_{1-4}$ alkyl, $C_{1-4}$ haloalkyl, $C_{1-4}$ alkoxy or $C_{1-4}$ haloalkoxy) or cyano.

In a still further aspect the present invention provides a compound of formula (I), wherein $R^1$ is $C_{2-4}$ alkenyl (especially vinyl) or $C_{2-4}$ alkynyl (especially ethynyl) either of which is optionally substituted by halogen, alkoxy (especially $C_{1-4}$ alkoxy), cycloalkyl (especially $C_{3-7}$ cycloalkyl, such as cyclopropyl or cyclohexyl), phenyl (optionally substituted by halogen), pyridinyl (optionally substituted by halogen) or cyano.

Specific compounds of formula (I) are presented in Table I below.

TABLE I

| Compound No. | Ar | R | $R^1$ |
|---|---|---|---|
| 1 | 5-Cl-pyridin-3-yl | $CH_2CF_3$ | CH(O) |
| 2 | 5-Cl-pyridin-3-yl | $CH_2CF_3$ | $CH=CCl_2$ |
| 3 | 5-Cl-pyridin-3-yl | $CH_2CF_3$ | $C\equiv CH$ |
| 4 | 5-Cl-pyridin-3-yl | $CH_2CF_3$ | $CH_2OH$ |
| 5 | 5-Cl-pyridin-3-yl | $CH_2CF_3$ | $C\equiv CCl$ |
| 6 | 5-Cl-pyridin-3-yl | $CH_2CF_3$ | H |
| 7 | 5-Cl-pyridin-3-yl | $CH_2CF_3$ | $CO_2H$ |
| 8 | 5-Cl-pyridin-3-yl | $CH_2CF_3$ | $CO_2CH_3$ |
| 9 | 5-Cl-pyridin-3-yl | $CH_2CF_3$ | CH=NOH |
| 10 | 5-Cl-pyridin-3-yl | $CH_2CF_3$ | $CH=NOCH_3$ |
| 11 | 5-Cl-pyridin-3-yl | $CH_2CF_3$ | $CH=C(CN)_2$ |
| 12 | 5-Cl-pyridin-3-yl | $CH_2CF_3$ | $CHF_2$ |
| 13 | 5-Cl-pyridin-3-yl | $CH_2CF_3$ | $CF_3$ |
| 14 | 5-Cl-pyridin-3-yl | $CH_2CF_3$ | $CH=CH_2$ |
| 15 | 5-Cl-pyridin-3-yl | $CH_2CF_3$ | CH=CH(cyclopropyl) |
| 16 | 5-Cl-pyridin-3-yl | $CH_2CF_3$ | $CH=CHOCH_3$ |
| 17 | 5-Cl-pyridin-3-yl | $CH_2CF_3$ | CH=CHCl (E) |
| 18 | 5-Cl-pyridin-3-yl | $CH_2CF_3$ | CH=CHCl (Z) |
| 19 | 5-Cl-pyridin-3-yl | $CH_2CF_3$ | $CH=CH(C_6H_5)$ |
| 20 | 5-Cl-pyridin-3-yl | $CH_2CF_3$ | CH=CHCN (E) |
| 21 | 5-Cl-pyridin-3-yl | $CH_2CF_3$ | $CH_2OCH_3$ |
| 22 | 5-Cl-pyridin-3-yl | $CH_2CF_3$ | $C\equiv C$(pyridin-3-yl) |
| 23 | 5-Cl-pyridin-3-yl | $CH_2CF_3$ | $C\equiv C(4-F-C_6H_4)$ |
| 24 | 5-Cl-pyridin-3-yl | $CH_2CF_3$ | $C\equiv C$(pyridin-2-yl) |
| 25 | 5-Cl-pyridin-3-yl | $CH_2CF_3$ | $CH_2OC(O)C(CH_3)_3$ |
| 26 | $3,5-F_2-C_6H_3$ | $CH_3$ | $CH_2NHC(O)CH_3$ |
| 27 | $3,5-F_2-C_6H_3$ | $CH_3$ | $CH_2NH_2$ |
| 28 | $3,5-F_2-C_6H_3$ | $CH_3$ | $CH_2NHC(O)(C_6H_5)$ |
| 29 | $3,5-F_2-C_6H_3$ | $CH_3$ | $NHC(O)OCH_3$ |
| 30 | pyridin-3-yl | $CH_3$ | $OCH_3$ |
| 31 | 6-Cl-pyridin-3-yl | $CO_2C(CH_3)_3$ | $OCH_3$ |
| 32 | 6-Cl-pyridin-3-yl | $CH_3$ | $OCH_3$ |
| 33 | pyridin-3-yl | $CO_2C(CH_3)_3$ | $OCH_3$ |
| 34 | 5-Cl-pyridin-3-yl | $CH_2CF_3$ | tetrazol-5-yl |
| 35 | 5-Cl-pyridin-3-yl | $CH_2CF_3$ | 5-$CH_3$-1,2,4-oxadiazol-3-yl |
| 36 | 5-Cl-pyridin-3-yl | $CH_2CF_3$ | $C(NH_2)=NOH$ |
| 37 | 5-Cl-pyridin-3-yl | $CO_2CH_2CH_3$ | $NH_2$ |
| 38 | 5-Cl-pyridin-3-yl | $CO_2CH_2CH_3$ | $CONH_2$ |
| 39 | 5-Cl-pyridin-3-yl | $CO_2CH_2CH_3$ | NHCHO |
| 40 | 5-Cl-pyridin-3-yl | $CO_2CH_2CH_3$ | $^+N\equiv C^-$ |
| 41 | 5-Cl-pyridin-3-yl | $CO_2CH_2CH_3$ | $NO_2$ |
| 42 | 5-Cl-pyridin-3-yl-N-oxide | $CO_2CH_2CH_3$ | $NO_2$ |
| 43 | $3,5-F_2-C_6H_3$ | $CO_2C(CH_3)_3$ | OH |
| 44 | 5-Cl-pyridin-3-yl | $CH_2CH=CH_2$ | $CH=CH_2$ |
| 45 | 5-CN-pyridin-3-yl | $CH_2CH=CH$ | $CH=CH_2$ |
| 46 | 5-Br-pyridin-3-yl | $CH_2CH=CCH_3$ | $CH=CH_2$ |
| 47 | 5-$CH_3O$-pyridin-3-yl | $CH_2CHF_2$ | $CH=CH_2$ |
| 48 | 5-acetylenyl-pyridin-3-yl | $CH_2CO_2CH_3$ | $CH=CH_2$ |
| 49 | 6-Cl-pyrazin-2-yl | $CH(CH_3)CO_2CH_3$ | $CH=CH_2$ |
| 50 | 6-$CH_3O$-pyrazin-2-yl | $CO_2CH_3$ | $CH=CH_2$ |
| 51 | 5-Cl-pyridin-3-yl | $CH_2CN$ | $CH=CH_2$ |
| 52 | 5-Cl-pyridin-3-yl | $CH_2CH_2CN$ | $CH=CH_2$ |
| 53 | 5-Cl-pyridin-3-yl | $CH_2C_6H_5$ | $CH=CH_2$ |
| 54 | 5-Cl-pyridin-3-yl | $CH_2CH_2CF_3$ | $CH=CH_2$ |
| 55 | 5-Cl-pyridin-3-yl | $CH_2CH(CH_3)_2$ | $CH=CH_2$ |
| 56 | 5-Cl-pyridin-3-yl | H | $CH=CH_2$ |

The preparation of the compounds of formula (I) may be accomplished by use of one or more of the synthetic techniques described below and further illustrated in the Examples.

The compounds of formula (I) can be prepared from compounds of formula (II) by reacting the compounds of formula (II) in ways described in the literature to convert a cyano group to an $R^1$ group or replace a cyano group with an $R^1$ group.

Compounds of formula (II) can also be prepared by treating compounds of formula (VI) with a suitable base, such as lithium diisopropylamide (LDA), and reacting the product so formed with a halide ArHal, wherein Hal is a halogen atom.

Compounds of formula (VI) can be prepared by treating 3-cyano-8-azabicyclo[3.2.1]octane (VII) with a suitable base, such as potassium carbonate, in the presence of a halide RL', wherein L' is a leaving group (especially halogen or triflate).

3-Cyano-8-azabicyclo[3.2.1]octane (VII) can be prepared by demethylating 3-cyano-8-methyl-8-azabicyclo[3.2.1] octane (IV) by, for example, treating them with a chloroformate ester (such as vinyl chloroformate) to produce a carbamate, and subjecting the product so formed to acid hydrolysis.

Alternatively, compounds of formula (VI) can be prepared by treating compounds of formula (VIII) with tosylmethyl isocyanide in the presence of a suitable base, such as potassium ethoxide.

Compounds of formula (VIII) can be prepared by the Robinson tropinone synthesis, see, for instance, J. Chem. Soc., (1917) 111, 762. Alternatively, compounds of formula (VIII) can be prepared by reacting cyclohepta-2,6-dienone (XI) with an amine, $RNH_2$, as described in, for example, Tetrahedron, (1973) 155, Bull. Chem. Chem. Soc. Jpn., (1971) 44, 1708 or J. Org. Chem., (1971) 36, 1718.

The compounds of formula (I) wherein R is methyl, can be prepared from compound of formula (III) by reacting the compounds of formula (III) in ways described in the literature to convert a cyano group to an $R^1$ group or replace a cyano group with an $R^1$ group.

Compounds of formula (III) can be prepared by treating 3-cyano-8-methyl-8-azabicyclo[3.2.1]octane (IV) with a suitable base, such as lithium diisopropylamide (LDA), and reacting the product so formed with a halide ArHal, wherein Hal is a halogen atom.

3-Cyano-8-methyl-8-azabicyclo[3.2.1]octane (IV) can be prepared by treating tropinone (V) with tosylmethyl isocyanide in the presence of a suitable base, such as potassium ethoxide. Alternatively, 3-cyano-8-methyl-8-azabicyclo [3.2.1]octane (IV) can be prepared by treating tropine (X) with thionyl chloride to give 3-chloro-8-methyl-8-azabicyclo[3.2.1]octane (XII) and reacting (XII) with cyanide as described in J. Am. Chem. Soc., (1958) 80, 4677.

The compounds of formula (IX) (that is compounds of formula (I) wherein $R^1$ is hydroxy) can be prepared by reacting compounds of formula (VIII) with a product obtainable by treating a compound of formula ArHal (wherein Hal is a halogen) with a suitable lithium species (such as n-butyl lithium).

The hydroxy group present in the compounds of formula (IX) can be further reacted by methods known in the art to prepare other compounds of formula (I).

In further aspects the present invention provides processes for preparing compounds of formula (I), as hereinbefore described.

In a further aspect the invention provides a method of combating insect and like pests at a locus by applying to the locus or the pests an insecticidally effective amount of an insecticidal composition comprising a compound of formula (I) or an acid addition salt, quaternary ammonium salt or N-oxide derived therefrom.

The compounds of formula (I) can be used to combat and control infestations of insect pests such as Lepidoptera, Diptera, Homoptera and Coleoptera (including Diabrotica i.e. corn rootworms) and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species which may be controlled by the compounds of formula (I) include: *Myzus persicae* (aphid), *Aphis gossypii* (aphid), *Aphis fabae* (aphid), *Aedes aegypti* (mosquito), Anopheles spp. (mosquitos), Culex spp. (mosquitos), *Dysdercus fasciatus* (capsid), *Musca domestica* (housefly), *Pieris brassicae* (white butterfly), *Plutella xylostella* (diamond back moth), *Phaedon cochleariae* (mustard beetle), Aonidiella spp. (scale insects), Trialeurodes spp. (white flies), *Bemisia tabaci* (white fly), *Blattella germanica* (cockroach), *Periplaneta americana* (cockroach), *Blatta orientalis* (cockroach) *Spodoptera littoralis* (cotton leafworm), *Heliothis virescens* (tobacco budworm) *Chortiocetes terminifera* (locust), Diabrotica spp. (rootworms), Agrotis spp. (cutworms), *Chilo partellus* (maize stem borer), *Nilaparvata lugens* (planthopper), *Nephotettix cincticeps* (leafhopper), *Panonychus ulmi* (European red mite), *Panonychus citri* (citrus red mite), *Tetranychus urticae* (two-spotted spider mite), *Tetranychus cinnabarinus* (carmine spider mite), *Phyllcoptruta oleivora* (citrus rust mite), *Polyphagotarsonemus latus* (broad mite) and Brevipalpus spp. (mites). Further examples include insects which adversely affect the health of the public at large and animals.

In order to apply the compounds of formula (I) to the locus of the nematode, insect or acarid pest, or to a plant susceptible to attack by the nematode, insect or acarid pest, the compound is usually formulated into a composition which includes in addition to a compound of formula (I) a suitable inert diluent or carrier material, and, optionally, a surface active agent. The amount of composition generally applied for the control of nematode pests gives a rate of active ingredient from 0.01 to 10 kg per hectare, preferably from 0.1 to 6 kg per hectare.

Thus in another aspect the present invention provides a insecticidal, acaricidal or nematicidal composition comprising an insecticidally, acaricidally or nematicidally effective amount of a compound of formula (I) and a suitable carrier or diluent therefor.

The compositions can be applied to the soil, plant or seed, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, Fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. In use, the concentrates are diluted in water and applied by means of a spray to the area to be treated.

Suitable liquid solvents for ECs include methyl ketones, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of disopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids; and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water dispersible powder WS) or liquids (flowable concentrate FS, liquid seed treatment LS, or microcapsule suspension CS) for use in seed treatments.

In use the compositions are applied to the insect pests, to the locus of the pests, to the habitat of the pests, or to growing plants liable to infestation by the pests, by any of the known means of applying pesticidal compositions, for example, by dusting, spraying, or incorporation of granules.

The compound of formula (I) may be the sole active ingredient of the composition or it may be admixed with one or more additional active ingredients such as insecticides, synergists, herbicides, fungicides or plant growth regulators where appropriate. Suitable additional active ingredients for inclusion in admixture with a compound of formula (I) may be compounds which will broaden the spectrum of activity of the compositions of the invention or increase their persistence in the location of the pest. They may synergise the activity of the compound of formula (I) or complement the activity for example by increasing the speed of effect or overcoming repellency. Additionally multi-component mixtures of this type may help to overcome or prevent the development of resistance to individual components. The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorfluazuron;

e) Organic tin compounds such as cyhexatin, fenbutatin oxide, azocyclotin;

f) Macrolides such as avermectins or milbemycins, for example such as abamectin, ivermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents;

k) Imidacloprid;

l) spinosad.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylron, cyromazine, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicide which can be included is propanil, an example of a plant growth regulator for use in cotton is "Pix", and examples of fungicides for use in rice include blasticides such as blasticidin-S. The ratio of the compound of formula (I) to the other active ingredient in the composition will depend upon a number of factors including type of target, effect required from the mixture etc. However in general, the additional active ingredient of the composition will be applied at about the rate at which it is usually employed, or at a slightly lower rate if synergism occurs.

The invention is illustrated by the following Examples. Examples 1–25 illustrate the preparation of a range of compounds of formula (I). Examples 26–33 illustrate compositions suitable for the application of the compounds of formula (I) according to the invention. The following ingredients are referred to by their Registered Trade Marks and have the composition as shown below.

| Registered Trade Mark | Composition |
| --- | --- |
| Synperonic NP8 }<br>Synperonic NP13 }<br>Synperonic OP10 } | Nonylphenol-ethylene oxide condensate |
| Aromasol H | Alkylbenzene solvent |
| Solvesso 200 | Inert organic diluent |
| Keltrol | Polysaccharide |

Throughout the Examples references to Compound Nos. refer to compounds numbered on Table I above. Selected NMR data and melting point data are presented in the Examples. For NMR data, no attempt has been made to list every absorption. The following abbreviations are used throughout the Examples:

| | |
| --- | --- |
| mp = melting point (uncorrected) | ppm = parts per million |
| s = singlet | t = triplet |
| m = multiplet | dd = double doublet |
| d = doublet | q = quartet |

EXAMPLE 1

This Example illustrates the preparation of exo-3-(5-chloropyrid-3-yl)-endo-3-formyl-8-(2,2,2-trifluoroethyl)-8-azabicyclo[3.2.1]octane (Compound No. 1).

Stage 1

A few drops of dilute hydrochloric acid were added to a solution of 2,5-dimethoxytetrahydrofuran (16.5 g) in water (70 ml). After stirring at room temperature for 30 minutes 2,2,2-trifluoroethylamine hydrochloride (16.9 g), acetonedicarboxylic acid (18.3 g) and sodium acetate (10.0 g) were added and the mixture stirred at room temperature for 2 days. The mixture was diluted to 500 ml with water, saturated with potassium carbonate and extracted with ethyl acetate (twice). The combined organic extracts were washed with aqueous potassium carbonate, dried (magnesium sulfate) and evaporated under reduced pressure. Distillation (90° C.; 0.1 mmHg) gave 8-(2,2,2-trifluoroethyl)-8-azabicyclo-[3.2.1]octan-3-one (8.7 g).

Stage 2

Potassium tert-butoxide (5.4 g) was added slowly with cooling to a stirred solution of 8-(2,2,2-trifluoroethyl)-8-azabicyclo[3.2.1]octan-3-one (4.0 g) and tosylmethyl isocyanide (4.9 g) in 1,2-dimethoxyethane (80 ml, dry) and ethanol (5 ml, dry) under nitrogen at such a rate so as to keep the temperature below 10° C. The mixture was stirred for 18 hours while allowing it to warm to room temperature, evaporated under reduced pressure and added to aqueous potassium carbonate solution. The mixture was extracted with ethyl acetate (twice) and the combined extracts were dried (magnesium sulfate) and evaporated under reduced pressure to give an oil. The mixture was extracted with hexane heated to 65° C. and the extracts allowed to cool and evaporated under reduced pressure to give exo-3-cyano-8-(2,2,2-trifluoroethyl)-8-azabicyclo[3.2.1]octane (2.5 g) mp 90–92° C.

Stage 3 exo-3-Cyano-8-(2,2,2-trifluoroethyl)-8-azabicyclo[3.2.1]octane (1.09 g) in tetrahydrofuran (10 ml) was added to a stirred solution of lithium disopropylamide [made by adding n-butyl lithium (2.4 ml of a solution in hexane, 2.5M) to diisopropylamine (0.61 g) in tetrahydrofuran (10 ml)] at −25° C. under nitrogen. After 2 hours at −25° C. the mixture was cooled to −76° C. and 3,5-dichloropyridine (0.74 g) in tetrahydrofuran (10 ml) added. The mixture was allowed to warm to room temperature, stirred for 18 hours and evaporated under reduced pressure. The mixture was dissolved in ether, washed with water (×2), dried (magnesium sulfate) and evaporated under reduced pressure. Chromatography [SiO$_2$; diethyl ether:hexane (20:80) to (50:50)] gave exo-3-(5-chloropyrid-3-yl)-endo-3-cyano-8-(2,2,2-trifluoroethyl)-8-azabicyclo [3.2.1]octane (0.45 g) mp 109.5–111.5° C.

Stage 4

The product from Stage 3 (4.5 g) was dissolved in diethyl ether (dry; 100 ml), cooled to −10° C. under an atmosphere of nitrogen and a solution of lithium aluminium hydride (30 ml of a solution in diethyl ether, 1M added slowly over 20 minutes to the vigorously stirred mixture, maintaining the reaction temperature at −10° C. On complete addition the reaction was stirred at −10 ° C. for 30 minutes, cooled to −76 ° C. and treated with water (30 ml) over 5 minutes allowing the temperature to gradually rise to −20° C. The ether soluble fraction was decanted from the white precipitate, which was washed with further ether (100 ml). The ether fractions were combined, washed with dilute aqueous sodium carbonate solution (100 ml), dried (magnesium sulfate), and evaporated under reduced pressure to give an oil. The oil was fractionated by chromatography (silica; hexane:ethyl acetate, 4:1) to give the required product as a colourless solid, 2.2 g, mp 100.5–101.5° C.

$^1$H NMR (CDCl$_3$):δ 1.50(2H,m); 1.90(2H,m); 2.25(2H, dd); 2.75(2H,dd); 2.85(2H,q); 3.50(2H,broad m); 7.50(1H, t); 8.35(1H,d); 8.45(1H,d); 9.40(1H,s)ppm.

EXAMPLE 2

This Example illustrates the preparation of exo-3-(5-chloropyrid-3-yl)-endo-3-(2,2-dichloroethenyl)-8-(2,2,2-trifluoroethyl)-8-azabicyclo [3.2.1]octane (Compound No. 2).

The product from Example 1, Stage 4 (2.0 g) in carbon tetrachloride (dry, 50 ml) containing triphenyl phosphine (8.3 g) was stirred and heated to reflux under an atmosphere of nitrogen for 9 hours and stored at ambient temperature for 18 hours. The solvent was evaporated under reduced pressure and the brown residue partitioned between aqueous sodium carbonate and ethyl acetate. The organic fraction was separated, dried (magnesium sulfate) and evaporated under reduced pressure. The residue was fractionated by chromatography (silica; 4:1 hexane:ethyl acetate) to give the required product as a light brown oil, 1.55 g.

$^1$H NMR (CDCl$_3$):δ 1.95(4H,m); 2.25(2H,dd); 2.45(2H, dd); 2.85(2H,q); 3.40(2H, broad m); 6.50(1H,s); 7.55(1H,t); 8.40(1H,d); 8.45(1H,d)ppm.

EXAMPLE 3

This Example illustrates the preparation of exo-3-(5-chloropyrid-3-yl)-endo-3-ethynyl-8-(2,2,2-trifluoroethyl)-8-azabicyclo[3.2.1]octane (Compound No. 3).

The product from Example 2 (0.2 g) was dissolved in tetrahydrofuran (dry, 3 ml) and cooled to −60° C. with stirring under an atmosphere of nitrogen. A solution of n-butyl lithium (0.47 ml of a solution in hexane, 2.5M was added over 1 hour, the reaction stirred for 1 hour at −60° C. and n-butanol (1 ml) added. The reaction was allowed to warm to ambient temperature and dilute aqueous sodium carbonate(5.0 ml) added. The mixture was extracted with ethyl acetate (2×5 ml), dried (magnesium sulfate) and evaporated under reduced pressure to give a yellow oil. The oil was fractionated by chromatography (silica; hexane:ethyl acetate 4:1) to give the required product as a pale brown oil, 0.075 g.

$^1$H NMR (CDCl$_3$): δ 1.90(2H,broad m); 2.20(2H,dd); 2.30(2H,dd); 2.40(1H,s); 2.50(2H,m); 2.85(2H,q); 3.40(2H, broad m); 7.85(1H,t); 8.45(1H,broad s); 8.70(1H,broad s)ppm.

EXAMPLE 4

This Example illustrates the preparation of exo-3-(5-chloropyrid-3-yl)-endo-3-hydroxymethyl-8-(2,2,2-trifluoroethyl)-8-azabicyclo[3.2.1]octane (Compound No. 4).

exo-3-(5-Chloropyrid-3-yl)-endo-3-formyl-8-(2,2,2-trifluoroethyl)-8-azabicyclo[3.2.1]octane (prepared as in Example 1, 0.10 g) was dissolved in anhydrous diethyl ether (1 ml) and stirred at 0° C. under nitrogen. Lithium aluminium hydride (0.2 ml of a solution in diethyl ether, 1.0M was added dropwise over 15 minutes, the reaction stirred for a further 30 minutes at 0° C. and allowed to warm to ambient temperature. After 30 minutes the reaction was treated with water (5 ml) and then ethyl acetate (10 ml) added. The organic fraction was separated, dried (magnesium sulfate) and evaporated to give an oil which was fractionated by preparative thick layer chromatography (silica, eluent: ethyl acetate) to give the required product, 0.054 g, as a colourless oil.

$^1$H NMR(CDCl$_3$): δ 1.80(2H,m); 2.00(2H,m); 2.15(4H, m); 2.85(2H,q); 3.40(2Hm); 3.65(2H,m); 7.50(1H,dd); 8.45 (1H,d); 8.50(1H,d)ppm.

EXAMPLE 5

This Example illustrates the preparation of exo-3-(5-chloropyrid-3-yl)-endo-3-(2-chloroethynyl)-8-(2,2,2-trifluoroethyl)-8-azabicyclo[3.2.1]octane (Compound No. 5).

The product from Example 2 (0.12 g) in methanol (1 ml) containing sodium methoxide (0.016 g) was stirred under nitrogen, heated to 60° C. for 10 minutes and allowed to cool to ambient temperature for 18 hours. Further sodium methoxide (0.1 g) was added and the mixture heated for 2 hours at 60° C. and cooled to ambient temperature. The mixture was poured into water (5 ml), extracted with ethyl acetate (5 ml) and the organic fraction dried (magnesium sulfate) and evaporated under reduced pressure to give an oil which was fractionated by preparative thick layer chromatography (silica; hexane:ethyl acetate 4:1 by volume) to give the required product as a colourless solid, 0.017 g, mp 74–6° C.

EXAMPLE 6

This Example illustrates the preparation of exo-3-(5-chloropyrid-3-yl)-8-(2,2,2-trifluoroethyl)-8-azabicyclo [3.2.1]octane (Compound No. 6).

exo-3-(5-Chloropyrid-3-yl)-endo-3-cyano-8-(2,2,2-trifluoroethyl)-8-azabicyclo[3.2.1]octane (0.2 g) was dissolved in dry tetrahydrofuran (2ml) and cooled to −10° C. with stirring under nitrogen. Lithium aluminium hydride (1 ml of a solution in tetrahydrofuran, 1M) was slowly added over 20 minutes and the reaction allowed to warm to ambient temperature and stored for 18 hours. The reaction was cooled to 0° C., treated with water (5 ml) and extracted with ethyl acetate (2×10 ml). The organic fractions were combined, dried (magnesium sulfate) and evaporated under reduced pressure to give a brown oil, 0.18 g, which was purified by chromatography (silica; hexane:ethyl acetate 3:1 by volume) to give the required product as a colourless solid, 0.025 g, mp104–5° C.

EXAMPLE 7

This Example illustrates the preparation of exo-3-(5-chloropyrid-3-yl)-endo-3-carboxy-8-(2,2,2-trifluoroethyl)-8-azabicyclo[3.2.1]octane (Compound No. 7).

Stage 1 exo-3-(5-Chloropyrid-3-yl)-endo-3-cyano-8-(2,2,2-trifluoroethyl)-8-azabicyclo-[3.2.1]octane (1.7 g) was dissolved in concentrated sulfuric acid (5 ml) and stored for 40 hours. The mixture was poured into ice/water (100 ml), basified with sodium hydroxide and extracted into ethyl acetate (200 ml), dried (magnesium sulfate) and evaporated under reduced pressure. The residue was recrystallised from a small volume of ethyl acetate to give exo-3-(5-chloropyrid-3-yl)-endo-3-carboxamido-8-(2,2,2-trifluoroethyl)-8-azabicyclo[3.2.1]octane as a colourless solid, 1.4 g, mp 233–4° C.

Stage 2

The product from Stage 1 (1.2 g) was finely powdered, stirred in acetonitrile (20 ml) at ambient temperature and treated portionwise with nitrosonium tetrafluoroborate (1.4 g). The suspension gradually dissolved to give a green solution which subsequently became yellow whilst gas was evolved from the reaction mixture. The reaction was stirred for 1 hour, heated to 50° C. for 5 minutes and cooled to ambient temperature. Water (2 ml) was added, the solvent evaporated under reduced pressure and the residue extracted with sodium hydroxide solution. The basic, aqueous fraction was washed with ethyl acetate (2×20 ml) and the aqueous fraction separated, taken to pH 7 with hydrochloric acid and extracted with ethyl acetate (2×20 ml). The combined organic fractions were dried (magnesium sulfate) and evaporated under reduced pressure to give the required product as a light brown solid, 0.3 g, mp 160–3° C.

EXAMPLE 8

This Example illustrates the preparation of exo-3-(5-chloropyrid-3-yl)-endo-3-carbomethoxy-8-(2,2,2-trifluoroethyl)-8-azabicyclo[3.2.1]octane (Compound No. 8).

The product from Example 7 (0.050 g) in acetone (2 ml) containing anhydrous potassium carbonate (0.1 g) and methyl iodide (0.027 g) were stirred at 60° C. in a sealed glass vessel for 2 hours. The solvent was evaporated and the residue was fractionated by preparative thick layer chromatography (silica; eluent ethyl acetate) to give the required product was obtained as a colourless solid, 0.023 g, mp 104–5° C.

EXAMPLE 9

This Example illustrates the preparation of exo-3-(5-chloropyrid-3-yl)-endo-3-(N-hydroxyiminomethy)-8-(2,2,2-trifluoroethyl)-8-azabicyclo[3.2.1]octane (Compound No. 9).

The aldehyde from Example 1 (0.075 g) in propan-2-ol (1 ml) was treated with a solution of hydroxylamine hydrochloride (0.20 g) in water (2 ml) and taken to pH 7 with 50% aqueous sodium hydroxide. The reaction was stirred at ambient temperature for 1 h, evaporated under reduced pressure and the residue treated with aqueous sodium carbonate and extracted into ethyl acetate (2×5 ml). The combined organic extracts were dried (magnesium sulfate) and evaporated under reduced pressure. The residue was fractionated by thick layer chromatography (silica; ethyl acetate) to give the required product as a colourless solid, 0.052 g, mp 133–5° C.

exo-3-(5-Chloropyrid-3-yl)-endo-3-(N-methoxyiminomethyl)-8-(2,2,2-trifluoroethyl)-8-azabicyclo[3.2.1]octane (Compound No. 10), (colourless solid, mp 94–5° C.), was prepared in a similar procedure using O-methyl hydroxylamine.

EXAMPLE 10

This Example illustrates the preparation of exo-3-(5-chloropyrid-3-yl)-endo-3-(2,2-dicyanoethenyl)-8-(2,2,2-trifluoroethyl)-8-azabicyclo [3.2.1]octane (Compound No. 11).

The aldehyde from Example 1 (0.33 g), malononitrile (5 ml) and ammonium acetate (0.1 g) were heated in a sealed glass vessel to 100° C. with stirring for 1 hour under an atmosphere of nitrogen. The reaction was poured into aqueous sodium carbonate solution and extracted with ethyl acetate (3×20 ml). The combined organic phase was washed with aqueous sodium carbonate solution (20 ml), dried (magnesium sulfate) and evaporated under reduced pressure to give a brown oil. The oil was fractionated by preparative thick layer chromatography (silica; 40% ethyl acetate:hexane) and the oil obtained heated to 125° C. at 1 mm Hg to remove traces of malononitrile to give the required product as a brown gum, 0.080 g.

$^1$H NMR (CDCl$_3$):δ 1.75(2H,m); 2.10(2H,m); 2.50(2H,dd); 2.75(2H,dd); 2.85(2H,q); 3.50(2H,broad signal); 7.60(1H,t); 7.65(1H,s); 8.40(1H,broad signal); 8.55(1H,broad signal)ppm.

EXAMPLE 11

This Example illustrates the preparation of exo-3-(5-chloropyrid-3-yl)-endo-3-difluoromethyl-8-(2,2,2-trifluoroethyl)-8-azabicyclo[3.2.1]octane (Compound No. 12).

The aldehyde from Example 1 (0.10 g) in diethylaminosulfurtrifluoride (1 ml) was stirred at 35° C. for 9 hours and stored at ambient temperature for 18 hours. The mixture was poured into ice/water (100 ml), basified with potassium carbonate, extracted with ethyl acetate (100 ml), dried (magnesium sulfate) and evaporated under reduced pressure to give an oil, 0.075 g. The oil was fractionated by chromatography (silica, hexane:tert-butyl methyl ether 4:1 by volume) to give the required product (0.006 g).

$^1$H NMR (CDCl$_3$):δ 1.70(2H,m); 2.10(2H,m); 2.35(4H, m); 2.85(2H,q); 3.45(2H,m); 6.00(1H,t,J=60Hz); 7.60(1H, dd); 8.40(1H,d); 8.50(1H,d)ppm.

EXAMPLE 12

This Example illustrates the preparation of exo-3-(5-chloropyrid-3-yl)-endo-3-trifluoromethyl-8-(2,2,2-trifluoroethyl)-8-azabicyclo[3.2.1]octane (Compound No. 13).

The acid from Example 7 (0.6 g) was dissolved in anhydrous hydrofluoric acid (9.6 g) in a Monel 400 autoclave. Sulfur tetrafluoride (6 g) was pressurised into the mixture which was gradually heated from ambient temperature to 100° C. for 12 hours. The autoclave was cooled in stages to −15° C. and the gases vented to waste. The residual brown solution was poured onto ice (50 g), the organic material extracted with dichloromethane (3×20 ml), the combined organic phase washed with water (twice), dried (magnesium sulfate) and evaporated under reduced pressure. The residue was treated with aqueous hydrochloric acid (40 ml, 2M) and washed with ethyl acetate (2×20 ml). The aqueous phase was basified with sodium carbonate, extracted with ethyl acetate (2×20 ml), dried (magnesium sulfate) and evaporated under reduced pressure to give the required product as a brown gum, 0.25 g.

$^1$H NMR (CDCl$_3$):δ 1.70(2H,m); 1.90(4H,m); 2.60(2H, q); 3.00(2H,dd); 3.45(2H,m); 7.75(1H,dd); 8.40(1H,d); 8.60(1H,d)ppm.

EXAMPLE 13

This Example illustrates the preparation of exo-3-(5-chloropyrid-3-yl)-endo-3-ethenyl-8-(2,2,2-trifluoroethyl)-8-azabicyclo[3.2.1]octane (Compound No. 14).

Methyl triphenyl phosphonium bromide (0.71 g) was suspended in dry tetrahydofuran (10 ml) and stirred under nitrogen at ambient temperature whilst a solution of lithium bis(trimethylsilyl) amide (2.0 ml of a solution in tetrahydrofuran, 1M) was slowly added. The yellow mixture was stirred for 20 minutes and the aldehyde from Example 1 (0.33 g) added. The reaction was heated to 40° C. for 10 minutes, treated with water (25 ml) and extracted with ethyl acetate (25 ml). The organic phase was separated, extracted with hydrochloric acid (2×25 ml, 2M) and the organic fraction discarded. The aqueous phase was made basic with sodium carbonate, extracted with diethyl ether (2×25 ml), dried (magnesium sulfate) and evaporated under reduced pressure to give the required product as an off-white solid, 0.29 g, mp 78–80° C.

The following analogues were made using a similar procedure:

exo-3-(5-Chloropyrid-3-yl)-endo-3-(E)-(2-cyclopropylethenyl)-8-(2,2,2-trifluoroethyl)-8-azabicyclo[3.2.1]octane (Compound no. 15), yellow oil; $^1$H NMR (CDCl$_3$): δ 0.05(2H,m); 0.35(2H,m); 0.75(1H,m); 1.65(2H,m); 1.85(2H,m); 2.05(4H,m);2.60(2H,q); 3.15(2H, m); 5.40(1H,t); 6.70(1H,d); 7.45(1H,broad signal); 8.15(1H,broad signal); 8.30(1H,broad signal)ppm.

(E) and (Z) (ratio 1:2)-exo-3-(5-Chloropyrid-3-yl)-endo-3-(2-methoxyethenyl)-8-(2,2,2-trifluoroethyl)-8-azabicyclo[3.2.1]octane (Compound No. 16), oil; $^1$H NMR (CDCl$_3$): δ 1.80–2.30(6H,m); 2.50(2H,dd); 2.85(2H,q); 3.35(2H, m); 3.50(3H,s); 4.60(isomer ,d); 5.00(E isomer,d); 5.80 (isomer,d); 6.30(E isomer,d); [7.50(dd); 7.60(dd); 8.35 (d); 8.40(d); 8.50(d) E/Z isomers]ppm.

exo-3-(5-Chloropyrid-3-yl)-endo-3-(E(2-chloroethenyl)-8-(2,2,2-trifluoroethyl)-8-azabicyclo[3.2.1]octane (Compound No. 17), oil; $^1$H NMR (CDCl$_3$): δ 1.90(4H, m); 2.10(2H,dd); 2.35(2H,dd); 2.80(2H,q); 3.40(2H, broad signal); 6.10(2H,m); 7.45(1H,t); 8.40(2H,m)ppm.

exo-3-(5-Chloropyrid-3-yl)-endo-3-(Z)(2-chloroethenyl)-8-(2,2,2-trifluoroethyl)-8-azabicyclo[3.2.1]octane (Compound No. 18), colourless solid, mp 96.0–98.5° C. Compounds 17 and 18 were separated by chromatography (silica; hexane/ethyl acetate 3:1 by volume) from a 2:1 mixture.

exo-3-(5-Chloropyrid-3-yl)-endo-3-(E)-(2-phenethenyl)-8-(2,2,2-iuoroethyl)-8-azabicyclo[3.2.1]octane (Compound No. 19), yellow oil; $^1$H NMR (CDCl$_3$): δ 1.90(4H,m); 2.40(4H,m); 2.90(2H,q); 3.40(2H,broad signal); 6.35(1H, d); 6.55(1H,d); 7.20–7.35(5H,m); 7.55(1H,dd); 8.35(1H, d); 8.45(1H,d)ppm.

exo-3-(5-Chloropyrid-3-yl)-endo-3-(E)-(2-cyanoethenyl)-8-(2,2,2-trifluoroethyl)-8-azabicyclo[3.2.]octane (Compound No. 20), colourless solid, mp 129–133° C.

EXAMPLE 14

This Example illustrates the preparation of exo-3-(5-chloropyrid-3-yl)-endo-3-methoxymethyl-8-(2,2,2-trifluoroethyl)-8-azabicyclo[3.2.1]octane (Compound No 21).

The alcohol from Example 4 (0.2 g) was dissolved with stirring in dimethyl sulfoxide (2 ml) containing powdered potassium hydroxide (1 g) and methyl iodide (1 ml) at ambient temperature. The red-brown mixture was stirred for 1 hour, poured into water (20 ml), extracted with diethyl ether (2×20 ml), dried (magnesium sulfate) and evaporated under reduced pressure to give a brown oil. The oil was fractionated by thick layer chromatography (silica; ethyl acetate) to give the required product, 0.03 g, as a colourless oil.

$^1$H NMR (CDCl$_3$):δ 1.80(2H,m); 2.00–2.25(6H,m); 2.85 (2H,q); 3.20(3H,s); 3.40(4H,broad signal); 7.50(1H,t); 8.40 (2H,dd)ppm.

EXAMPLE 15

This Example illustrates the preparation of exo-3-(5-chloropyrid-3-yl)-endo-3-(2-(pyrid-3-yl)ethynyl)-8-(2,2,2-trifluoroethyl)-8-azabicyclo[3.2.1]octane (Compound No. 22).

The alkyne from Example 3 (0.38 g), 3-bromopyridine (0.5 g), tetrakis(triphenyl-phosphine) palladium (O) (0.05 g, catalyst), copper bromide (0.05 g, catalyst), in triethylamine (1 ml) were stirred at 40° C. under an atmosphere of nitrogen for 30 minutes. The mixture was evaporated under reduced pressure, extracted with ethyl acetate (50 ml) and washed with sodium carbonate solution. The organic phase was extracted with hydrochloric acid (2×25 ml, 2M and the aqueous phase separated. The aqueous phase was washed with ethyl acetate (2×25 ml), basified with sodium carbonate solution and the aqueous phase re-extracted with ethyl acetate (2×50 ml). The combined organic phase extracts were dried (magnesium sulfate) and evaporated under reduced pressure to give a yellow oil which was fractionated by preparative thick layer chromotography (silica; ethyl acetate) to give the required product as an off-white solid, 0.10 g, mp 115.0–119.5° C.

$^1$H NMR (CDCl$_3$): δ 2.00(2H,m); 2.30(4H,m); 2.50(2H, m); 2.90(2H,m); 3.50(2H,m), 7.20(1H,dd); 7.70(1H,double triplet); 7.80(1H,t); 8.50(1H,d); 8.55(1Hdd); 8.70(1H,d); 8.80(1H,d)ppm.

The following analogues were prepared using a similar procedure:

exo-3-(5-Chloropyrid-3-yl)-endo-3-(2-(4-fluorophenyl) ethynyl)-8-(2,2,2-trifluoroethyl)-8-azabicyclo[3.2.1] octane (Compound No 23), brown solid , mp 96–101° C. $^1$H NMR (CDCl$_3$):δ 2.00(2H,m); 2.30(4H,m); 2.60(2H, m); 2.90(2H,q); 3.50(2H,m); 7.00(2H,m); 7.40(2H,m); 7.85(1H,dd); 8.45(1H,d); 8.80(1H,d)ppm.

exo-3-(5-Chloropyrid-3-yl)-endo-3-(2-(pyrid-2-yl)ethynyl)-8-(2,2,2-trifluoroethyl)-8-azabicyclo[3.2.1]octane (Compound No. 24), brown solid, mp 110–114° C.

EXAMPLE 16

This Example illustrates the preparation of exo-3-(5-chloropyrid-3-yl)-endo-3-pivaloyloxymethyl-8-(2,2,2-trifluoroethyl)-8-azabicyclo[3.2.1]octane (Compound No. 25).

The alcohol from Example 4 (0.2 g) was dissolved in dichloromethane (dry; 8 ml) and treated with pivaloyl chloride (0.086 ml) and N,N-diisopropylethylamine (0.12 ml) at ambient temperature. The mixture was stirred for 22 hours, heated to reflux for 6 hours and allowed to cool to ambient temperature for 18 hours. The reaction was treated with water (50 ml) and extracted with ethyl acetate (50 ml). The mixture was acidified with hydrochloric acid (50 ml, 2M) and the acidic fraction collected. The organic phase was further treated with hydrochloric acid (50 ml, 2M) and the aqueous, acidic fractions combined and washed with ethyl acetate. The aqueous fraction was separated, basified with sodium hydrogen carbonate solution and extracted with ethyl acetate (2×50 ml). The organic phase extracts were combined, dried (magnesium sulfate) and evaporated under reduced pressure to give a brown oil which solidified on cooling. The solid was washed with a small volume of 20% diethyl ether in hexane to give the required product as an off-white solid, 0.13 g, mp 155–157° C.

EXAMPLE 17

This Example illustrates the preparation of exo-3-(3,5-difluorophenyl)-endo-3-(N-acetylaminomethyl)-8-(methyl)-8-azabicyclo[3.2.1]octane (Compound No. 26).

Stage 1

Potassium tert-butoxide (22.4 g) was added portionwise to a stirred mixture of tropinone (11.58 g) and tosylmethyl isocyanide (21.2 g) in dry 1,2-dimethoxyethane (240 ml) and ethanol (8 ml) at 0° C. under an atmosphere of nitrogen at such a rate to maintain the reaction temperature between 0° C. and 10° C. The mixture was allowed to warm to room temperature and stirred for a further 4 hours. After standing the mixture at room temperature for 3 days it was filtered and the solid residue washed with 1,2-dimethoxyethane. The filtrate was evaporated under reduced pressure and fractionated by chromatography [silica, 10% methanol in dichloromethane) to give exo-3-cyano-8-methyl-8-azabicyclo[3.2.1]octane (9.1 g).

Stage 2 exo-3-Cyano-8-methyl-8-azabicyclo[3.2.1]octane (13.6 g) in dry tetrahydrofuran (80 ml) was added dropwise to a stirred solution of lithium diispropylamide [made by adding n-butyl lithium (40 ml of a solution in hexane, 2.5M) to diisopropylamine (14.0 ml) in tetrahydrofuran (80 ml)] at −25° C. under an atmosphere of nitrogen. The mixture was stirred at −25° C. for 0.5 hours and cooled to −78° C. 1,3,5-Trifluorobenzene (12.0 g) in tetrahydrofuran (80 ml)

was added dropwise at such a rate to maintain the temperature below −65° C. The mixture was allowed to warm to room temperature overnight and then poured into water and extracted with dichloromethane. The combined extracts were washed with brine, dried (MgSO$_4$) and evaporated under reduced pressure to give a yellow solid. This was recrystallised from diethyl ether to give exo-3-(3,5-fluorophenyl)-endo-3-cyano-8-methyl-8-azabicyclo[3.2.1] octane. The mother liquor from the recrystallisation was chromatographed [silica, 10% methanol in dichloromethane] to give further desired product, giving a total yield of 11.2 g.

Stage 3

The product from Stage 2 (2.5 g) in dry diethyl ether (15 ml) was stirred at 0° C. under an atmosphere of nitrogen, lithium aluminium hydride (15.3 ml of a diethyl ether solution, 1.0M) was added dropwise and the reaction was stirred for a further 30 minutes. The reaction was allowed to warm to ambient temperature and stored for 18 hours. The mixture was re-cooled to 0° C., quenched with a mixture of methanol/water/acetic acid (8:2:1), stirred for 1.5 hours, diluted with aqueous sodium chloride solution and made basic with aqueous sodium hydroxide (2M). The mixture was extracted with dichloromethane, dried (magnesium sulfate) and evaporated under reduced pressure and the residue fractionated by chromatography (silica, dichloromethane:methanol) to give exo-3-(3,5-difluorophenyl)-endo-3-aminomethyl-8-methyl-8-azabicyclo[3.2.1]octane, 1.9 g, mp 113–7° C. (Compound No. 27).

Stage 4

The product from Stage 3 (0.5 g) was dissolved in dry diethyl ether (10 ml) containing dry triethylamine (0.26 ml) at 0° C. with stirring and treated with acetyl chloride (0.15 g). The reaction was stirred at 0° C. for 1 hour, allowed to warm to ambient temperature and the mixture extracted with dichloromethane. The extract was washed with aqueous sodium chloride solution, water, dried (magnesium sulfate) and evaporated under reduced pressure to give the required product as a yellow solid, 0.35 g, mp 56.5–57.2° C.

exo-3-(3,5-Difluorophenyl)-endo-3-(N-benzoylaminomethyl)-8-methyl-8-azabicyclo[3.2.]octane (Compound No. 28), colourless solid, mp 149.3° C., was prepared in a similar way using benzoyl chloride.

EXAMPLE 18

This Example illustrates the preparation of exo-3-(3,5-difluorophenyl)-endo-3-carbomethoxyamino-8-methyl-8-azabicyclo[3.2.1]octane (Compound No. 29).

The carboxamide from Example 7, Stage 1 (0.56 g) was dissolved in methanol (10 ml) containing sodium methoxide (0.325 g) at ambient temperature with stirring. Bromine (0.11 ml) was added to the solution and the mixture stirred for 2 hours. The solvent was evaporated under reduced pressure and the residue extracted with diethyl ether (200 ml). The organic phase was washed with water, dried (magnesium sulfate) and evaporated under reduced pressure to leave a residue. The residue was fractionated by chromatography (silica, 20% methanol in dichloromethane) to give the required product, 0.16 g, mp 120–2° C.

EXAMPLE 19

This Example illustrates the preparation of exo-3-(pyrid-3-yl)-endo-3-methoxy-8-methyl-8-azabicyclo[3.2.1]octane (Compound No. 30).

Stage 1

2-Chloro-5-aminopyridine (15.0 g) was dissolved in concentrated hydrochloric acid (150 ml) at 0° C. with stirring. Sodium nitrite (10.47 g) in water (5 ml) was added dropwise maintaining the reaction below 5° C. Sodium iodide (26.23 g) in water (20 ml) was slowly added to the orange solution at 0–5° C. and stirred for 1 hour and allowed to warm to ambient temperature over 18 hours. The reaction was diluted with water (300 ml), the solid which had formed filtered from solution and dissolved in ethyl acetate. The organic phase was washed with dilute aqueous sodium hydroxide, aqueous sodium hydrogen carbonate, dried (magnesium sulfate) and evaporated under reduced pressure. The residue was fractionated by chromatography (silica hexanel 5–10% ethyl acetate) to give 2-chloro-5-iodopyridine, 14.9 g, as a colourless solid, mp 89–90° C.

Stage 2

N-Carboethoxytropinone (1.0 g) was dissolved with stirring in dry chloroform (2.5 ml), cooled to 0° C. under an atmosphere of nitrogen and treated with trimethylsilyl iodide (1.22 g). The mixture was heated to reflux for 5 hours, stored at ambient temperature for 2 days and re-cooled to 0° C. under an atmosphere of nitrogen with stirring. The reaction was treated dropwise with a solution of hydrogen chloride in methanol (2.0 ml, 5M), stirred for 1.5 hours and evaporated under reduced pressure. The brown solid obtained was treated with toluene and the resulting mixture evaporated under reduced pressure. The residual solid was suspended in dry dichloromethane (5 ml), cooled to 0° C. under an atmosphere of nitrogen and a solution of pyridine (1.0 g) and 4-N,N-dimethylaminopyridine (5 mg, catalyst) in dichloromethane (5 ml) added. The solution was stirred for 0.5 hour, di-tert-butyl dicarbonate (1.43 g) added dropwise and the reaction allowed to warm to ambient temperature. The mixture was treated with water, extracted with dichloromethane and the combined organic phase washed with aqueous copper sulfate, water and aqueous sodium chloride, dried (magnesium sulfate) and evaporated under reduced pressure. The brown oil obtained was fractionated by chromatography (silica, 30%ethyl acetate/hexane) to give N-carbo-tert-butoxy-tropinone as a pale yellow solid, 0.91 g, mp 65.0–66.5° C.

Stage 3

2-Chloro-5-iodopyridine (0.32 g) was dissolved in a 2:1 mixture of diethyl ether and tetrahydrofuran (12 ml), cooled to −78° C. under an atmosphere of nitrogen with stirring and treated dropwise with n-butyl lithium (0.53 ml of a solution in hexane, 2.5M). The deep red solution was stirred at −78° C. for 20 minutes, and N-carbo-tert-butoxy-tropinone (0.30 g) in diethyl ether (3 ml) was added dropwise, after which the reaction mixture was allowed to warm to ambient temperature slowly over 18 hours. Saturated, aqueous ammonium chloride solution was added and the mixture extracted (3 times) with ethyl acetate. The combined organic phase was dried (magnesium sulfate) and evaporated under reduced pressure to give a gum which was fractionated by chromatography (silica, hexane:ethyl acetate, 1:1) to give exo-3-(6-chloropyrid-3-yl)-endo-3-hydroxy-8-(N-carbo-tert-butoxy)-8-azabicyclo[3.2.1]-octane (Compound No. 43) as a yellow, foamy solid, 0.24 g.

$^1$H NMR (CDCl$_3$):δ 1.45(9H,s); 1.75–1.95(2H,m); 1.95–2.10(2H,m); 2.10–2.50(5H,m); 4.2–4.4(2H,m); 7.25 (1H,d); 7.65(1H,dd); 8.40(1H,d)ppm.

Stage 4

The product from Stage 3 (0.10 g) was added to a suspension of sodium hydride (0.15 g) in dry tetrahydrofuran (5 ml) at 0° C. under an atmosphere of nitrogen, stirred for 1 hour and methyl iodide (0.046 g) was added. The reaction was stirred for 2 hours, further methyl iodide (0.02 ml) added and the reaction stored at ambient temperature for 2 days. The mixture was treated with water, extracted with ethyl acetate (3 times), the combined organic phase was washed with saturated sodium chloride solution, dried (magnesium sulfate) and evaporated under reduced pressure to give an oil. The residue was fractionated by chromatography (silica; 25% ethyl acetate in hexane) to give exo-3-(6-chloropyrid-3-yl)-endo-3-methoxy-8-(N-carbo-tert-butoxy)-8-azabicyclo[3.2.1]octane (Compound No. 31), 0.056 g, yellow oil.

$^1$H NMR (CDCl$_3$): δ 1.45(9H,s); 1.90–2.25(8H,m); 4.20 (1H,m); 4.35(1H,m); 3.0(3H,s); 7.30(1H,d); 7.60(1H,dd); 8.35(1H,d)ppm.

Stage 5

The product from Stage 4 (0.174 g) was dissolved in methanol (3.5 ml) containing potassium hydroxide (0.028 g) and 5% palladium on charcoal (0.174 g, catalyst) added. The mixture was stirred under an atmosphere of hydrogen for 18 hours, after which time the required hydrogenolysis was complete. The mixture was filtered, the filtrate evaporated under reduced pressure and the residue extracted into ethyl acetate. The organic phase was washed with saturated sodium chloride solution, dried (magnesium sulfate) and evaporated under reduced pressure to give exo-3-(pyrid-3-yl)-endo-3-methoxy-8-(N-carbo-tert-butoxy)-8-azabicyclo [3.2.1]octane (Compound No. 33), oil, 0.125 g.

$^1$H NMR (CDCl$_3$): δ 1.40(9H,s); 1.90–2.35(8H,m); 3.0 (3H,s); 4.25(1H,m); 4.35(1H,m); 7.25(1H,dd); 7.65(1H, double triplet), 8.60(1H,broad signal)ppm.

Stage 6

The product from Stage 5 (0.11 g) was dissolved in formic acid (3.5 ml), heated to reflux for 1 hour and cooled to ambient temperature. The mixture was treated with paraformaldehyde (0.12 g) and heated to reflux with stirring for 2 hours and stored at ambient temperature for 2 days. The reaction was evaporated under reduced pressure and the residue partioned between dichloromethane and aqueous sodium hydroxide solution. The phases were separated, the aqueous phase was re-extracted with dichloromethane and the combined organic phase was dried (magnesium sulfate) and evaporated under reduced pressure to give exo-3-(pyrid-3-yl)-endo-3-methoxy-8-methyl-8-azabicyclo[3.2.1]octane as a yellow oil, 0.073 g.

$^1$H NMR (CDCl$_3$):δ 2.0–2.35(8H,m); 2.40(3H,s); 2.95 (3H,s); 3.30(2H,m); 7.30(1H,dd); 7.70(1H,double triplet); 8.50(1H,dd); 8.65(1H,d)ppm.

In a similar procedure to Example 19, Stage 6 exo-3-(6-chloropyrid-3-yl)-endo-3-methoxy-8-(N-carbo-tert-butoxy)-8-azabicyclo[3.2.1]octane was converted to exo-3-(6-chloropyrid-3-yl)-endo-3-methoxy-8-methyl-8-azabicyclo[3.2.1]octane, (Compound No. 32), yellow oil; $^1$H NMR (CDCl$_3$): δ 1.95–2.15(8H,m); 2.35(3H,s); 2.95(3H,s); 3.25(2H,m); 7.30(1H,d); 7.65(1H,dd); 8.40(1H,d)ppm.

EXAMPLE 20

This Example illustrates the preparation of exo-3-(5-chloropyrid-3-yl)-endo-3-(tetrazol-5-yl)-8-(2,2,2-trifluoroethyl)-8-azabicyclo[3.2.1]octane (Compound No. 34).

exo-3-(5-Chloropyrid-3-yl)-endo-3-cyano-8-(2,2,2-uoroethyl)-8-azabicyclo[3.2.1]octane (prepared in Example 1 stage 3, 0.50 g) was dissolved in dry N,N-dimethylformamide (5.0 ml) containing sodium azide (0.13 g) and ammonium chloride (0.05 g, catalyst) with stirring and heated to 110° C. in a sealed glass vessel for 43 hours. The mixture was evaporated under reduced pressure and the residue treated with an aqueous solution of ammonium chloride, extracted with ethyl acetate (2×10 ml), dried (magnesium sulfate) and evaporated under reduced pressure to give a colourless gum. The gum was fractionated by preparative thick layer chromatography (silica; diethyl ether) to give the required product as a colourless solid, 0.13 g, mp 221–222° C.(dec).

$^1$H NMR (CDCl$_3$):δ 1.25(4H,m); 1.75(1H,m); 2.10(2H, d); 2.85(2H,q); 3.25(2H,d); 3.45(2H,m); 7.80(1H,m); 8.25 (1H,m); 8.40(1H,m)ppm. Molecular ion 372.

EXAMPLE 21

This Example illustrates the preparation of exo-3-(5-chloropyrid-3-yl)-endo-3-(5-methyl-1,2,4-oxadiazol-3-yl)-8-(2,2,2-trifluoroethyl)-8-azabicyclo[3.2.1]octane (Compound No. 35).

Stage 1 exo-3-(5-Chloropyrid-3-yl)-endo-3-cyano-8-(2,2,2-trifluoroethyl)-8-azabicyclo-[3.2.1]octane (prepared in Example 1 stage 3, 0.10 g) was added to a mixture of hydroxylamine hydrochloride (0.15 g) and potassium tert-butoxide (0.28 g) in tert-butanol (2 ml) with stirring under an atmosphere of nitrogen. The mixture was heated to 90–100° C. for 20 hours, the mixture cooled, evaporated under reduced pressure and the residue treated with aqueous ammonium chloride. The product was extracted into ethyl acetate (2×10 ml), dried (magnesium sulfate) and evaporated under reduced pressure to give a colourless oil. The oil was fractionated by preparative thick layer chromatography (silica; diethyl ether) to give endo-3-(3-amidoximido)-exo-3-(5-chloropyrid-3-yl)-8-(2,2,2-trifluoroethyl)-8-azabicyclo [3.2.1]octane (Compound No. 36) as a colourless foamy solid, (0.050 g), mp 167–169° C.

Stage 2

The product from Stage 1 (0.050 g) was dissolved in toluene (dry, 2 ml) containing acetic anhydride (0.018 g) with stirring. The mixture was heated to 80° C. for 0.5 hour, then at 110° C. for 11 hours. The mixture was evaporated under reduced pressure and the residue fractionated by preparative thick layer chromatography (silica; diethyl ether) to give the title product as a colourless solid, 0.026 g, mp 106–108° C.

$^1$H NMR (CDCl$_3$): δ 1.50(2H,q); 1.75(2H,m); 2.40(2H, dd); 2.55(3H,s); 2.85(2H,q); 3.15(2H,dd); 3.40(2H,m); 7.35 (1H,t); 8.40(1H, m); 8.50(1H, m)ppm.

EXAMPLE 22

This Example illustrates the preparation of endo-3-amino-8-(carboethoxy)-exo-3-(5-chloropyrid-3-yl)-8-azabicyclo [3.2.1]octane (Compound No. 37).

Stage 1

8-(Carboethoxy)-exo-3-(5-chloropyrid-3-yl)-endo-3-cyano-8-azabicyclo[3.2.1]octane (prepared, for example, as in WO 96/37494, 6.6 g) was dissolved in concentrated sulfuric acid (40 ml) containing water (10 ml) and stirred at 50° C. for 24 hours. Further concentrated sulfuric acid (20 ml) was added and the mixture heated for an additional 7 hours at 50° C. The reaction mixture was poured into water (500 ml), basified with aqueous sodium hydroxide and the product extracted with ethyl acetate (200 ml) and tert-butyl methyl ether (200 ml). The extracts were combined, dried (magnesium sulfate) and evaporated under reduced pressure to give endo-8-(carboethoxy)-3-carboxamido-exo-3-(5-chloropyrid-3-yl)-8-azabicyclo[3.2.1]octane (Compound No.38) as a colourless solid (2.65 g). A sample was recrystallised from ethyl acetate to give a colourless solid, mp 220.0–222.5° C.

Stage 2

The product from Stage 1 (0.10 g) was added to a solution of lithium hydroxide (0.072 g) in water (2 ml) and 1,4-dioxane (2 ml) and the mixture stirred at 40° C. Bromine (0.096 g) was added to the mixture in one portion and the reaction stirred for 1 hour at 40° C. The volatiles were evaporated under reduced pressure and the yellow residue extracted into ethanol (5 ml). The ethanolic solution was evaporated under reduced pressure to give a yellow semi-solid, which was extracted with hot ethyl acetate (10 ml). The extracts were evaporated under reduced pressure to give a yellow oil. The oil was fractionated by preparative thick layer chromatography (silica; ethyl acetate) to give the title product as a pale yellow oil, 0.036 g.

$^1$H NMR (CDCl$_3$):δ 1.30(3H,t); 1.80(2H,d); 1.95–2.15 (2H,m); 2.20–2.45(4H,m); 4.20(2H,q); 4.30(2H,m); 7.55 (1H,t); 8.40(1H,d); 8.50(1H,d)ppm.

EXAMPLE 23

This Example illustrates the preparation of 8-(carboethoxy)-exo-3-(5-chloropyrid-3-yl)-endo-3-N-formylamino-8-azabicyclo[3.2.1]octane (Compound No. 39).

endo-3-Amino-8-(carboethoxy)-exo-3-(5-chloropyrid-3-yl)-8-azabicyclo[3.2.1]octane (1.00 g) and formic acid (10 ml, 98%) were stirred and heated to reflux for 5 hours. The excess formic acid was evaporated under reduced pressure, the residue was treated with toluene (2×50 ml), each time evaporating under reduced pressure to remove residual formic acid. The residue was fractionated by eluting through a column of silica with ethyl acetate followed by preparative thick layer chromatography (basic alumina; ethyl acetate) to give the required product as a colourless solid, 0.19 g, mp 186.5–188.5° C.

$^1$H NMR (CDCl$_3$):δ 1.30(3H,t); 2.0–2.80(8H,m); 4.15 (2H,q); 4.45 (2H,m); 6.75(1H,m); 7.65(1H,t); 8.15(1H,m); 8.50(1H,d); 8.40(1H,d)ppm.

EXAMPLE 24

This Example illustrates the preparation of 8-(carboethoxy)-exo-3-(5-chloropyrid-3-yl)-endo-3-isocyano-8-azabicyclo[3.2.1]octane (Compound No. 40).

8-(Carboethoxy)-exo-3-(5-chloropyrid-3-yl)-endo-3-N-formylamino-[3.2.1]octane (0.15 g) was dissolved in dry dichloromethane (10 ml,) containing triethylamine (0.5 ml) and the stirred mixture was cooled to 0° C. Phosphorus oxychloride (0.5 ml) was added dropwise and the reaction stirred at 0° C. for 3 hours. The mixture was then evaporated under reduced pressure. The residue was treated with an aqueous solution of sodium bicarbonate and the product extracted into ethyl acetate (2×10 ml), the organic extracts were combined, dried (magnesium sulfate) and evaporated under reduced pressure to give a brown gum. The gum was fractionated by preparative thick layer chromatography (silica; ethyl acetate) to give the required product, 0.12 g, colourless gum.

$^1$H NMR (CDCl$_3$): δ 1.30(3H,t); 2.10–2.50(8H,m); 4.20 (2H,q); 4.50(2H,m); 7.75(1H,t); 8.55(2H,t)ppm.

EXAMPLE 25

This Example illustrates the preparation of 8-(carboethoxy)-exo-3-(5-chloropyrid-3-yl)-endo-3-nitro-8-azabicyclo[3.2.1]octane (Compound No. 41).

Stage 1

Acetonitrile (90 ml) containing water (9 ml) was stirred in a glass reaction vessel, cooled to −10° C. and purged with nitrogen. Fluorine diluted with nitrogen was slowly bubbled into the mixture, at a rate of 5 ml of fluorine per minute, for 0.5 hour and sodium fluoride (5.0 g) added to the solution. The mixture was stirred for 10 minutes at −5° C., cooled to −15° C. and endo-3-amino-8-carbethoxy-exo-3-(5-chloropyrid-3-yl)-8-azabicyclo[3.2.1]-octane (0.5 g) in dichloromethane (8 ml) was added and the mixture stirred for 10 minutes. The reaction mixture was poured into water (500 ml), basified with sodium hydrogen carbonate and extracted with dichloromethane (3×20 ml). The extracts were combined, washed with water, dried (magnesium sulfate) and evaporated under reduced pressure. The residue was fractionated by preparative thick layer chromatography (silica; 10% methanol by volume in ethyl acetate) to give 8-(carboethoxy)-exo-3-(5-chloropyrid-3-yl-1-oxide)-endo-3-nitro-8-azabicyclo[3.2.1]octane (Compound No. 42) as a colourless solid, 0.11 g, mp 217° C. (dec).

$^1$H NMR (CDCl$_3$): δ 1.25(3H,t); 1.70(2H,m); 2.00(2H, m); 2.40(2H,m); 3.45(2H,d); 4.15(2H,m); 4.45(2H,m); 7.30 (1H,t); 8.20(1H,d); 8.25(1H,d)ppm.

Stage 2

The product from Stage 1 (0.050 g) was dissolved in chloroform (2 ml) with stirring and phosphorus trichloride (0.2 ml) was added. The mixture was heated to 60° C. in a sealed glass vessel for 2 hours, cooled to ambient temperature and extracted with chloroform (5 ml). The extract was treated with a solution of aqueous sodium carbonate, the organic phase separated, dried (magnesium sulfate) and evaporated under reduced pressure to give the title product, 0.039 g, oil.

$^1$H NMR (CDCl$_3$):δ 1.25(3H,t); 1.70(2H,m); 2.00(2H,m); 2.45(2H,m); 3.55(2H,m); 4.15(2H,q); 4.45(2H,m); 7.70(1H, t); 8.45(1H,m); 8.50(1H,m)ppm. Molecular ion 339.

EXAMPLE 26

This Example illustrates an emulsifiable concentrate composition which is readily convertible by dilution with water into a liquid preparation suitable for spraying purposes. The concentrate has the following composition:

|  | % Weight |
|---|---|
| Compound No. 1 | 25.5 |
| SYNPERONIC NP13 | 2.5 |
| Calcium dodecylbenzenenesulphonate | 2.5 |
| AROMASOL H | 70 |

EXAMPLE 27

This Example illustrates a wettable powder composition which is readily convertible by dilution with water into a liquid preparation suitable for spraying purposes. The wettable powder has the following composition:

|  | % Weight |
|---|---|
| Compound No. 13 | 25.0 |
| Silica | 25.0 |
| Sodium lignosulphonate | 5.0 |

-continued

| | % Weight |
|---|---|
| Sodium lauryl sulphate | 2.0 |
| Kaolinite | 43.0 |

EXAMPLE 28

This Example illustrates a dusting powder which may be applied directly to plants or other surfaces and comprises 1% by weight of Compound No. 25 and 99% by weight of talc.

EXAMPLE 29

This Example illustrates a concentrated liquid formulation suitable for application by ultra low volume techniques after mixing with paraffinic diluents.

| | % Weight |
|---|---|
| Compound No. 29 | 90.0 |
| SOLVESSO 200 | 10.0 |

EXAMPLE 30

This Example illustrates a capsule suspension concentrate which is readily convertible by dilution with water to form a preparation suitable for application as an aqueous spray.

| | % Weight |
|---|---|
| Compound No. 43 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccliaride (e.g. KELTROL) | 0.1 |
| Water | 76.4 |

EXAMPLE 31

A ready for use granular formulation:

| | % Weight |
|---|---|
| Compound No. 4 | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 32

An aqueous suspension concentrate:

| | % Weight |
|---|---|
| Compound No. 8 | 5.0 |
| Kaolinite | 15.0 |

-continued

| | % Weight |
|---|---|
| Sodium lignosulphonate | 3.0 |
| nonylphenolethoxylate (eg Synperonic NP8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 33

This Example illustrates a water dispersible granule formulation.

| | % Weight |
|---|---|
| Compound No. 20 | 5 |
| Silica | 5 |
| Sodium lignosulphate | 10 |
| Sodium dioctylsulphosuccinate | 5 |
| Sodium acetate | 10 |
| Montmorillonite powder | 65 |

EXAMPLE 34

This Example illustrates the insecticidal properties of the compounds of formula (I). The activity of the compounds of formula (I) was determined using a variety of pests. The pests were treated with a liquid composition containing 500 parts per million (ppm) by weight of the compound unless otherwise stated. The compositions were made by dissolving the compound in acetone and ethanol (50:50) mixture and diluting the solutions with water containing 0.05% by weight of a wetting agent sold under the trade name "SYNPERONIC" NP8 until the liquid composition contained the required concentration of the compound. "SYNPERONIC" is a Registered Trade Mark.

The test procedure adopted with regard to each pest was basically the same and comprised supporting a number of the pests on a medium which was usually a substrate, a host plant or a foodstuff on which the pests feed, and treating either or both the medium and the pests with the compositions. The mortality of the pests was then assessed at periods usually varying from two to five days after the treatment.

The results of the tests against peach aphid (*Myzus persicae*) are presented below. The results indicate a grading of mortality (score) designated as A, B or C wherein C indicates less than 40% mortality, B indicates 40–79% mortality and A indicates 80–100% mortality; "-" indicates that either the compound was not tested or no meaningful result was obtained. In this test Chinese cabbage leaves were infested with aphids, the infested leaves were sprayed with the test composition, and the mortality assessed after 3 days. Compound Nos. 1, 2, 3, 5, 6, 8, 9, 10, 11, 12, 14, 15, 16, 17, 18, 19, 20, 21, 23, 24, 28, 37 and 40 gave a mortality score of A.

In addition, in a similar test against red spider mites (*Tetranychus urticae*) Compounds Nos. 2, 3, 5, 8, 14, 16, 18, 21, 26, 28, 33 and 40 gave a mortality score of A.

Chemical Formulae Used in the Description

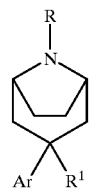
(I)

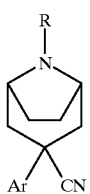
(II)

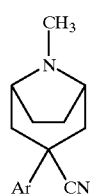
(III)

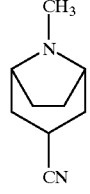
(IV)

(V)

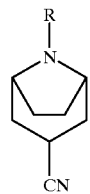
(VI)

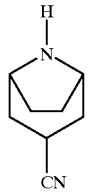
(VII)

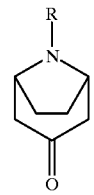
(VIII)

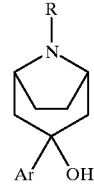
(IX)

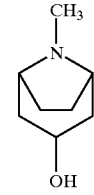
(X)

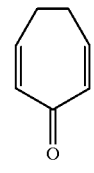
(XI)

(XII)

What is claimed is:
1. A compound of formula (I):

(I)

wherein Ar is optionally substituted phenyl, wherein the substutuents, if present, are selected from halogen atoms, cyano, alkyl, alkenyl, alkynyl, alkoxy, haloalkyl, haloalkenyl, alkylthio and alkyl amino groups; R represents hydrogen or cyano or a group selected from alkyl, aryl, heteroaryl, aralkyl, heteroarylalkyl, alkenyl, aralkenyl, alkynyl, alkoxycarbonyl, alkanesulfonyl, arenesulfonyl, alkenyloxycarbonyl, aralkyloxycarbonyl, aryloxycarbonyl, heterocyclylalkyl, carbamyl, dithiocarboxyl or $XR^3$ (where X represents oxygen or a group $NR^4$), provided that when R is alkenyl, aralkenyl or alkynyl said group does not have an unsaturated carbon atom bonding directly to the ring nitrogen of formula (I); $R^3$ and $R^4$ are, independently, hydrogen, alkyl, aryl, heteroaryl, aralkyl, heteroarylalkyl, alkenyl, aralkenyl, alkynyl, heterocyclylalkyl, alkoxycarbonyl or carboxylic acyl; alkyl moieties of R, $R^3$ and $R^4$ comprise from 1 to 15 carbon atoms, and are optionally substituted with one or more substituents selected from halogen, cyano, carboxyl, carboxylic acyl, carbamyl, alkoxycarbonyl, alkoxy, alkylenedioxy, hydroxy, nitro, amino, acylamino, imidate and phosphonato groups; aryl, heteroaryl, aralkyl, heteroarylalkyl, alkenyl, aralkenyl, alkynyl, alkoxycarbonyl, alkanesulfonyl, arenesulfonyl, alkanyloxycarbonyl, aralkyloxycarbonyl, aryloxycarbonyl, heterocyclylalkyl, carbarnyl or dithiocarboxyl moieties of R, $R^3$ and $R^4$ comprise from 1 to 15 carbon atoms, and are optionally substituted with one or more substituents selected from, halogen, cyano, carboxyl, carboxylic acyl, carbamyl, alkoxycarbonyl, alkoxy, alkylenedioxy, hydroxy, nitro, haloalkyl, alkyl, amino, acylamino, imidate and phosphonato groups; $R^1$ represents hydrogen, hydroxy, alkyl, alkoxy, amino, nitro, isocyanato, acylamino, hydroxyalkyl, optionally substituted heteroaryl, alkoxyalkyl, haloalkyl, halohydroxyalkyl, aralkyloxyalkyl, acyloxyalkyl, amidoximido, sulfonyloxyalkyl, aminoalkyl, alkoxycarbonylamino, acylaminoalkyl, cyanoalkyl, imino, formyl, acyl or carboxylic acid or an ester or amide thereof, or alkenyl or alkynyl either of which is optionally substituted by halogen, alkoxy, cycloalkyl, optionally substituted aryl, optionally substituted heteroaryl or cyano; or an acid addition salt, quaternary ammonium salt or N-oxide derived therefrom; provided that, when $R^1$ is H or OH then R is not H, $CH_3$, CN or benzyl; when $R^1$ is OH or O-lower alkanoyl of up to 4 carbon atoms, R is not optionally substituted benzofuranalkyl or optionally substituted benzothiophenealkyl; and when $R^1$ is OH then R is not —$(CH_2)_3$XAr, where X is —C(O), CH(CN), CH(OH), O, S, NH, C(CN)(4-fluorophenyl), CH(4-fluorophenyl) or C(OH)(4-fluorophenyl) and Ar is 2-thienyl, 2-furyl, 4-pyridyl or optionally substituted phenyl.

2. A compound of formula (I) as claimed in claim 1 wherein Ar is a substituted phenyl, wherein the substitutents are selected from halogen, $C_{1-4}$ alkyl, $C_{1-4}$ alkoxy, $C_{2-4}$ alkynyl or cyano.

3. A compound of formula (I) as claimed in claim 1 wherein R is $C_{1-4}$ alkyl, $C_{2-4}$ haloalkyl (the α-carbon being unsubstituted) or $C_{1-4}$ alkoxycarbonyl.

4. A compound of formula (I) as claimed in claim 1 wherein $R^1$ is $C_{2-4}$ alkenyl or $C_{2-4}$ alkynyl either of which is optionally substituted by halogen, alkoxy, cycloalkyl, phenyl (optionally substituted by halogen), pyridinyl (optionally substituted by halogen) or cyano.

5. An insecticidal, acaricidal or nematicidal composition comprising an insecticidally, acaricidally or nematicidally effective amount of a compound of formula (I) as claimed in claim 1 and a suitable carrier or diluent therefor.

6. A method of combating and controlling insect, acarine or nematode pests at a locus which comprises treating the pests or the locus of the pests with a pesticidally effective amount of a compound of formula (I) as claimed in claim 1.

7. A method of combating and controlling insect, acarine or nematode pests at a locus which comprises treating the pests or the locus of the pests with a pesticidally effective amount of a composition according to claim 5.

8. A method according to claim 7 wherein the pests are insect pests of growing plants.

9. A method according to claim 8 wherein the pests are insect pests of growing plants.

* * * * *